US00PP30060P2

(12) United States Plant Patent
Lane

(10) Patent No.: US PP30,060 P2
(45) Date of Patent: Jan. 8, 2019

(54) ***MALUS* PLANT NAMED 'SPA766'**

(50) Latin Name: *Malus domestica*
Varietal Denomination: SPA766

(71) Applicant: Her Majesty the Queen in Right of Canada as represented by the Minister of Agriculture and Agri-Food, Ottawa (CA)

(72) Inventor: William David Lane, Summerland (CA)

(73) Assignee: HER MAJESTY THE QUEEN IN RIGHT OF CANADA AS REPRESENTED BY THE MINISTER OF AGRICULTURE AND AGRI-FOOD, Ottawa (CA)

( * ) Notice: Subject to any disclaimer, the term of this patent is extended or adjusted under 35 U.S.C. 154(b) by 43 days.

(21) Appl. No.: 15/530,321

(22) Filed: Dec. 22, 2016

Related U.S. Application Data

(60) Provisional application No. 62/387,313, filed on Dec. 23, 2015.

(51) Int. Cl.
*A01H 5/08* (2018.01)

(52) U.S. Cl.
USPC ..... Plt./161

(58) Field of Classification Search
USPC ..... Plt./156, 161
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of apple tree, 'SPA766', that is characterized by its fruit with skin that has a red over color with prominent medium sized lenticels, its fruit that is crisp with a pleasant tasting, its fruit that has a medium storage period, and its weak vigor.

1 Drawing Sheet

Botanical classification: *Malus domestica.*
Varietal denomination: 'SPA766'.

BACKGROUND OF THE INVENTION

The present invention relates to a new and distinct cultivar of apple tree, botanically known as *Malus domestica* 'SPA766', referred to hereafter by its cultivar name, 'SPA766'.

The new cultivar arose from a cross made by the Inventor in Summerland, British Columbia, Canada in 1992 between an unnamed, proprietary plant in the Inventor's breeding program, reference no. 11W-16-016 as the female parent and *Malus domestica* 'Chinook' (U.S. Plant Pat. No. 10,669) as the male parent. The Inventor selected 'SPA766' as a single unique plant amongst the seedlings that resulted from the above cross in 1999.

Asexual propagation of the new cultivar was first accomplished by vegetative budding in 2000 under the direction of the Inventor in Summerland, BC, Canada. Asexual propagation by vegetative budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPA766' as a unique cultivar of apple tree.

1. 'SPA766' exhibits fruit with skin that has a red over color with prominent medium sized lenticels.
2. 'SPA766' exhibits fruit that is crisp with a pleasant taste.

3. 'SPA766' exhibits fruit that has a medium storage period.
4. 'SPA766' exhibits weak vigor.

The female parent of 'SPA766', reference no. 11W-16-016, differs from 'SPA766' in having fruit lenticels that are less pronounced and in having fruit that has a lighter red over color. The male parent, 'Chinook', is similar to 'SPA766' in having red fruit that is firm, crisp and pleasant tasting. 'Chinook' differs from 'SPA766' in having fruit that is smaller in size and different in shape. 'SPA766' can also be compared to the cultivar 'Royal Gala' (U.S. Plant Pat. No. 4,121). 'Royal Gala' is similar to 'SPA766' in having red fruit that is similar in shape. 'Royal Gala' differs from 'SPA766' in having fruit that is lighter red in color, in having less percentage of over color on the fruit and in having lenticels that are less prominent.

BRIEF DESCRIPTION OF THE DRAWING

The accompanying colored photograph illustrates the overall appearance and distinct characteristics of the new apple tree. The photograph was taken of fruit on a 10 year-old plant of 'SPA766' as grown outdoors in the ground in Summerland, BC, Canada.

The photograph in FIG. 1 provides a close-up view of the fruit and foliage of 'SPA766'.

The colors in the photographs are as close as possible with the photographic and printing technology utilized and the color values cited in the detailed botanical description accurately describe the colors of the new apple tree.

DETAILED BOTANICAL DESCRIPTION

The following is a detailed description of the new apple variety as observed on four year-old plants as grown outdoors in the ground in Summerland, BC, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Tree description:

*Plant type*.—Deciduous fruiting tree.

*Plant habit*.—Spreading.

*Height and spread*.—An average of 2.1 m in height and 160 cm in width.

*Cold hardiness*.—At least to U.S.D.A. Zone 4.

*Diseases and pests*.—Similar susceptibility and resistance to diseases as other *Malus domestica* varieties.

*Propagation*.—Vegetative budding and grafting.

*Roots*.—Fibrous, Brown Group 200B in color, grown on rootstock.

*Root development*.—1 year (time to produce a young plant from budding).

*Growth rate*.—Weak.

Description of branches:

*Frequency*.—Medium.

*Angle*.—Approximately 50° angle to trunk.

*Bearing*.—Predominance of bearing on spurs.

*Bark color*.—Black Group 202C with underlying Greyed-Orange 164A.

Description of one year-old shoots:

*Pubescence on upper one year-old shoot*.—Weak to medium on upper side.

*Shine of bark*.—Moderate.

*Flexibility*.—Medium to strong.

*Thickness of shoot at center of middle internode*.—Average of 3.8 mm.

*Bark color* (*using bark on* 1 *year old shoots exposed to sun*).—Greyed-Orange Group 175A.

*Shoot angle*.—Approximately 60°.

*Lenticels*.—Circular in shape, 1.2 mm in length and diameter, 21 per sq. cm, color Greyed-Yellow Group 161D.

Description of growing shoots:

*Color of growing tip of shoot*.—Yellow-Green Group 147C.

*Shape of shoot tips leaves in cross section*.—Concave.

*Pubescence of shoot tip leaves*.—Weak on upper surface.

*Color of shoot tip leaves*.—Yellow-Green Group 147C on lower surface and Yellow-Green Group 146B on upper surface.

*Distribution of color other than green on shoot tips leaves*.—None.

Leaf description:

*Leaf orientation*.—Upward.

*Leaf division*.—Simple.

*Leaf shape*.—Ovate.

*Leaf size*.—Average of 8.9 cm in length and 4.5 cm in width.

*Leaf apex*.—Cuspidate.

*Leaf base*.—Oblique or obtuse.

*Leaf surface*.—Upper surface; slightly glossy, lower surface; moderately pubescent.

*Leaf margin*.—Serrate.

*Leaf color*.—Upper surface Green Group 137A, lower surface Green Group 138B.

*Leaf anthocyanin on lower surface*.—None.

*Leaf venation*.—Pinnate main veins with netted minor veins, Green Group 142B on upper and lower surface.

*Petiole size*.—Average of 2.4 cm in length and 1.3 mm in diameter.

*Petiole color*.—Green Group 142B with a tinge of anthocyanin at base Greyed-Purple Group 184B.

*Stipules*.—Small to medium in size (mean 0.64 cm in length), found on actively growing shoots where they are present on newly developed leaves but sometimes abscising on older leaves.

Flower description:

*Blooming period*.—Mid-season; early to mid-May in British Columbia, Canada.

*Number of flowers*.—Average of 5 per spur.

*Inflorescence type*.—Corymb of rotate flowers.

*Flower buds*.—At pink tip stage; Red-purple Group 61B in color, Elliptic with an Obtuse tip in shape.

*Flower size*.—Average of 4.5 cm in diameter and 1.4 cm in depth.

*Flower fragrance*.—Mild.

*Flower aspect*.—Upright.

*Petals*.—5 per flower, unfused, sometimes overlapping, ovate in shape, obtuse apex, round base, entire margin, about 2.1 cm in length and 1.5 cm in width, color of upper surface when opening and mature; White Group 155D with tinges of Red-Purple Group 64B, color of lower surface when opening and mature; White 155D with tinges of Red-Purple Group 64B, upper and lower surface glabrous, slight to moderately pubescent on both surfaces.

*Sepals*.—Color lower surface Yellow-Green Group 144A, color upper surface Yellow-Green Group 144A, tinged with Red-Purple 64B, slight to moderately pubescent on both surfaces, Linear in shape, entire margin, acute apex, touching to overlapping at base, average of 8.8 mm in length (medium) and 2.7 mm in width.

*Pedicel*.—Yellow-Green Group 144A tinged with Greyed-Purple Group 184B in color on side exposed to sun, average of 2.6 cm in length and 1.1 mm in width, glabrous surface.

*Pistil*.—Compound carpel with 5 stigmas fused at base, 15.1 mm in length, style is Green Group 142C in color and 13.1 mm in length, stigma is Greyed-Yellow Group 162A in color, ovary is pubescent and Green Group 139A in color.

*Stamens*.—Average of 20, anther is oblong in shape, White 155A in color and 10.4 mm in length, pollen is Yellow Group 11B in color and moderate in quantity.

*Pollination requirement*.—Cross pollination required.

Fruit description:

*Fruit size*.—Medium, 8.4 cm in diameter, average of 8.0 cm in height.

*Position of maximum diameter*.—Midway between proximal and distal ends.

*Fruit shape*.—Globose.

*Fruit symmetry*.—Symmetrical.

*Fruit prominence of ribbing*.—Not present.

*Fruit aperture of eye*.—Open, an average of 6.2 mm in diameter.

*Persistence of calyx*.—Persistent.

*Length of sepal*.—Average of 7.4 mm.

*Spacing of sepals at base*.—Touching to overlapping.
*Eye basin*.—Deep and broad, an average of 9.5 mm in depth and 30.7 mm in width.
*Stalk*.—Thin to medium thickness, an average of 2.7 mm thick and 20.8 mm in length.
*Depth of stalk cavity*.—Broad and medium depth, an average of 21.9 mm in depth, and 37.2 mm in width.
*Relief of surface*.—Smooth.
*Skin*.—Medium waxiness, bloom not present, texture; translucent, thin, and smooth.
*Skin color*.—Red Group 45A.
*Presence of russet*.—Very low to low level on cheeks.
*Lenticels*.—Small to medium (average of <1 mm), slightly prominent, Orange-Red Group 31D.
*Color of flesh*.—Yellow Group 11D.
*Distinctness of core line*.—Medium.
*Aperture of locules*.—Moderately open.
*Fruit set*.—Intermediate to good.
*Fruit maturity date*.—Early season, average harvest date is August 29th in Summerland, BC, Canada.
*Browning of flesh*.—Medium to strong.
*Firmness* (*without skin*).—Firm to very firm. (17.35 lbs).
*Texture of flesh*.—Firm.
*Cropping frequency*.—Annual to sometimes biennial.
*Fruit yield*.—11.1 kg/tree (slender spindle).
*Acidity*.—An average of 0.62 g/L titratable acidity (malic acid equivalent).
*Brix*.—An average of 13.6%.
*Seed*.—Ranges from Greyed-Orange Group 166C to Brown Group 200C in color when dry, ovoid to somewhat deltoid in shape, an average of 8.9 mm in length and 4.7 mm in width and 2.8 mm in thickness.
*Storage life*.—Minimum 3-4 months in common storage (average temperature of 34° F.).
*Market use*.—Fresh fruit.

It is claimed:

1. A new and distinct variety of apple tree named 'SPA766' as herein illustrated and described.

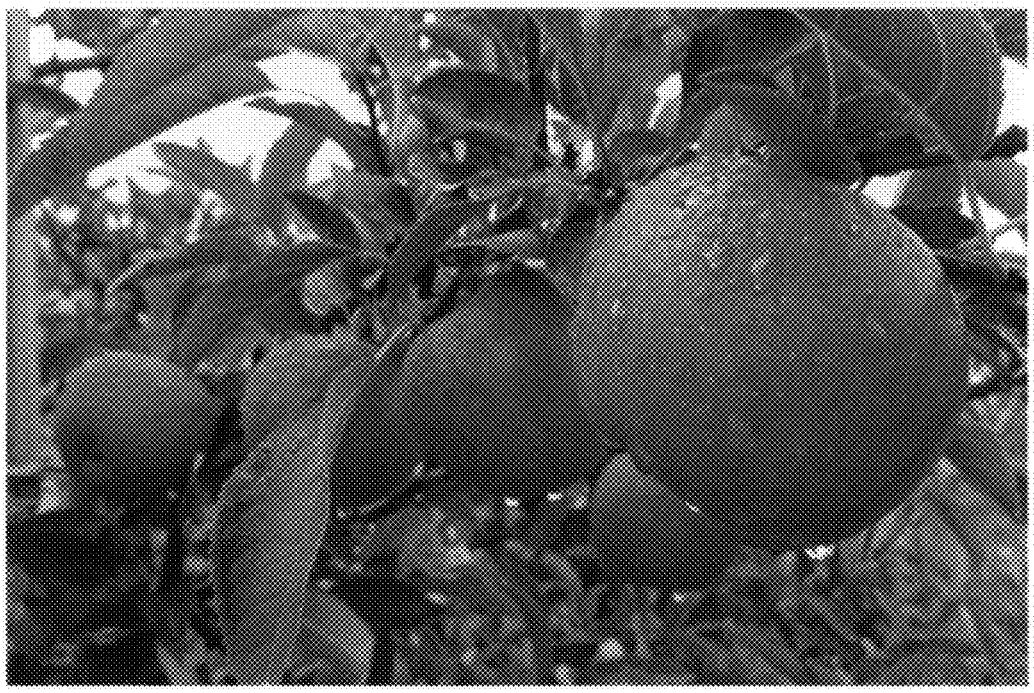

* * * * *